United States Patent [19]

Iwamoto

[11] Patent Number: 5,212,018
[45] Date of Patent: May 18, 1993

[54] CONDUCTIVITY METER AND METHOD OF PRODUCING AN ELECTRODE FOR USE IN SAME

[75] Inventor: Yasukazu Iwamoto, Miyanohigashi, Japan

[73] Assignee: Horiba, Ltd., Kyoto, Japan

[21] Appl. No.: 639,661

[22] Filed: Jan. 9, 1991

[30] Foreign Application Priority Data

Jan. 19, 1990 [JP]  Japan ................................... 2-10923

[51] Int. Cl.⁵ ......................... B22F 7/04; G01N 27/30
[52] U.S. Cl. .................................... 428/559; 428/553; 422/82.02; 204/290 F
[58] Field of Search .............................. 428/553, 559; 422/82.02; 324/439; 204/290 F

[56] References Cited

U.S. PATENT DOCUMENTS

| | | | |
|---|---|---|---|
| 3,014,166 | 12/1961 | Keblusek et al. | 252/62.2 |
| 3,107,172 | 10/1963 | Capp | 428/553 |
| 3,133,872 | 5/1964 | Miller et al. | 204/290 F |
| 4,444,641 | 4/1984 | Oda et al. | 204/286 |

OTHER PUBLICATIONS

Barrow, "Physical Chemistry", McGraw-Hill, pp. 22-1.

*Primary Examiner*—Donald P. Walsh
*Assistant Examiner*—Daniel Jenkins
*Attorney, Agent, or Firm*—Price, Gess & Ubell

[57] ABSTRACT

An improved electrode for a conductivity meter is provided formed of a titanium material cladded with platinum. The electrode is formed by immersing the titanium electrode form in an acid bath at an elevated temperature for approximately three hours. The surface of the electrode form is reduced in a relatively weak acid bath, and is then cladded by electrolysis with a platinum material to form a platinum black plating.

6 Claims, 2 Drawing Sheets

CONDUCTIVITY METER AND METHOD OF PRODUCING AN ELECTRODE FOR USE IN SAME

BACKGROUND OF THE INVENTION

1. Field of the Invention

The present invention relates to a conductivity meter for measuring a conductivity of a solution and, more particularly, to an improved electrode and a method of producing the same.

2. Description of Related Art

An alternating bielectrode conductivity meter has been known in the prior art as an instrument suitable for the measurement of the concentration of a solution and the like. This conductivity meter comprises two electrodes provided in a sensor portion. The electrodes are immersed in the solution to be measured, and an alternating voltage is applied between the electrodes to determine a value of resistance of the solution, by measuring a conductivity, which is a reciprocal of the value of resistance of the solution.

In a measurement of conductivity according to an alternative bielectrode method, charges are separated on a boundary surface of the metallic electrode and the solution. Thus, in the case where a condenser capacity (polarization capacity) is created in a solution having a high concentration, a polarization phenomenon can create a remarkably high error and can reduce the accuracy of the measurement of conductivity. To counter this effect, a conventional conductivity meter has resorted to platinum (Pt) as electrodes, and has subjected Pt electrodes to a platinum black plating.

It has been known that an equivalent circuit of electrodes is composed of an RC series circuit, and it is necessary to increase a loss coefficient D expressed by the following equation in order to reduce the polarization phenomenon of electrodes (D∞→the polarized resistance ingredient=0).

$$D = 2\pi f \cdot C \cdot R$$

wherein f is a frequency applied from the instrument, C is a condenser portion on the boundary surface of the electrodes and the solution, and R is an interelectrode resistance.

However, in order to increase the loss coefficient D on the basis of the above-described relationship, it is necessary to increase either the frequency f, the condenser portion C, or the interelectrode resistance R. A cell constant of the electrodes is usually unchanged, so that an increase of the interelectrode resistance R is limited, and an increase of the frequency f is also limited. Thus, it is necessary for the condenser portion C to be capable of increasing a surface area of the electrodes. The above-described conventional conductivity meter has been constructed by paying attention to this point.

Thus, it has been known that if Pt is subjected to the platinum black plating, the condenser portion C is increased and the surface area of the electrodes can be increased by hundreds of time to that which existed before the platinum black plating. In short, the polarization phenomenon can be reduced by increasing the loss coefficient D.

However, a disadvantage occurs in that Pt is not only difficult to process, but it is also expensive and, as a result, the conductivity meter becomes expensive. In addition, when Pt is subjected to platinum black plating, usually Pt particles are deposited on a mirror-like surface of the electrodes without any presurface treatment. Thus, a problem can occur in that the gilt formed by the platinum black plating is apt to be separated during the operation and cannot provide a long-term use. Furthermore, a problem has also occurred in that lead wires, such as copper wires, are difficult to connect with the Pt electrodes. Thus, the prior art is still seeking a relatively inexpensive electrode with high measurement accuracy for a conductivity meter.

SUMMARY OF THE INVENTION

The present invention has been achieved in view of the above-described problems, and it is an object of the present invention to provide a conductivity meter capable of reducing the polarization phenomenon and extending a measuring range by providing a method capable of forming electrodes with a reduced incidence of separation of a plated coat on the electrode substrate, in spite of the use of inexpensive electrode materials.

In order to achieve the above-described object, a conductivity meter provided with at least a pair of electrodes at suitable intervals on an electrode-supporting member, according to the present invention, is characterized in that titanium, subjected to a platinum black plating, is used as an electrode material for the electrodes.

In addition, a method of producing electrode material according to the present invention is characterized in that a titanium electrode substrate form is immersed in 3 N-HCl for an appointed time period at 90°-100° C. to acid treat a surface thereof. The titanium electrode form is then immersed in 0.1 N-HCl at normal room temperature, followed by a preelectrolysis by supplying a constant electrical current of 20 mA/cm² with platinum as a counter electrode. Subsequently titanium and platinum, as counter electrodes, are immersed in a plating bath containing a 3%-aqueous solution of chloroplatinic acid kept at 60° to 65° C. to subject the titanium electrode form to the platinum black plating at a specific resistance of the plating bath of 10 to 20 Ω·cm, an electrolytic voltage of about 2 V, and a supply current of 80 to 90 mA.

With the above-described construction, the titanium electrode form, subjected to the platinum black plating, is used as the electrodes of the conductivity meter, so that the condenser portion is increased in the surface area on the electrodes. Thus, any polarization phenomenon leading to an error in measurement can be greatly reduced to permit a measurement of the value of resistance of the solution with high accuracy, thereby permitting an accurate measurement of the conductivity, which has a reciprocal relationship to the value of resistance, in the measurement of a highly conductive solution and the like.

In addition, since the electrode material of the electrodes is titanium, it is relatively inexpensive and is easier to process. Moreover, a surface of titanium can be subjected to a pretreatment, and then a preelectrolysis followed by depositing platinum particles on a rough surface of titanium in the platinum black plating of titanium, so that a strong platinum black plated coat can be formed.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an improved electrode and method of making the same for a conductivity meter.

One preferred embodiment of the present invention will be below described with reference to the drawings.

Figure 1:
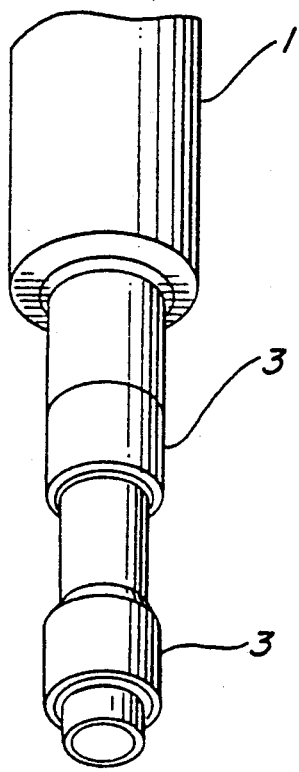
FIG. 1 is a perspective view showing the main parts of a sensor of a conductivity meter.

Referring to FIG. 1, a conductivity meter sensor portion is shown according to the present invention, and includes an electrode-supporting member 1 provided with a pair of electrodes 3, 3 disposed at a suitable interval.

Figure 2A:
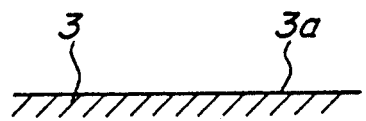
FIGS. 2(a) to (d) are schematic diagrams describing a plating process.

Next, a method of producing the electrodes 3, 3 of FIG. 1 is described. Titanium (Ti), stainless steel (SUS), nickel (Ni) and the like can be used as an electrode material of the electrode substrates, but it is preferred to use Ti and Ti alloys, for example, a titanium of the second grade (JIS H4680, commonly called "TB35"), which are superior in corrosion resistance, inexpensive, and easy to process. A surface of a Ti substrate is first subjected to an acid etching pretreatment in order to prepare it for a platinum black plating. This permits a subsequent formation of a strong plated coat on Ti. The Ti substrate is immersed for three hours in a 3 N-HCl solution kept at a temperature of 90° to 100° C., and then washed with pure water. Thus, the surface 3a of Ti, which originally had a mirror-like surface finish, as shown in FIG. 2(a), is etched to be turned into a rough surface of about hundreds of meshes. A chemical reaction at this time is expressed as follows:

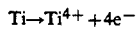

$$Ti \rightarrow Ti^{4+} + 4e^-$$

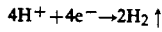

$$4H^+ + 4e^- \rightarrow 2H_2 \uparrow$$

Figure 2B:
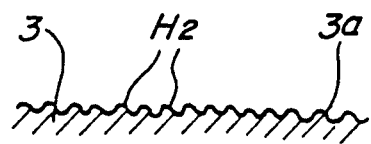
Figure 2C:
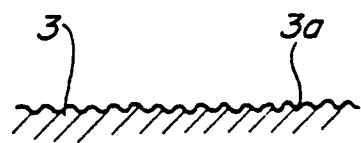

Thus, upon immersing the Ti substrate in the 3 N-HCl solution, the surface 3a of Ti is etched with a hot acid. During this time, a hydrogen gas is also rapidly generated because a hydrogen ion catches an electron. Thereupon, the hydrogen gas is adhered to the rough surface 3a of Ti to be occluded, as shown in FIG. 2(b).

Successively, a preelectrolysis is conducted to remove the hydrogen gas ($H_2$), but in this pretreatment an oxidized coating is formed on the etched surface 3a of Ti to hinder the formation of a plated coat, so that it is necessary to remove the oxidized coat by a reduction process. In the present preferred embodiment, the Ti substrate is immersed in 0.1 N-NCl at a normal room temperature with platinum (Pt) as a counter electrode. The Ti substrate is supplied with a constant current of 20 mA/cm² to conduct an electrolysis (reduction) for about five minutes. Thereupon, the hydrogen gas ($H_2$), which has been occluded in the surface 3a of Ti, is removed, and the oxidized coat is also removed to make the formation of a close or tight plated coat possible.

Subsequently, the Ti substrate is subjected to an electrolysis (reduction) to prepare it for the platinum black plating. During this time, the Ti substrate and the Pt electrode, as the counter electrode, are immersed in a plating bath containing a 3%-aqueous solution of a chloroplatinic acid kept at 60° to 65° C. A + side of a direct current power source is connected with the Pt electrode and a − side with the Ti substrate, to thereby supply them with a constant current of 80 to 90 mA for about 20 minutes, thereby performing the reduction process. During this time, in order to closely deposit Pt particles on Ti, it is necessary to set the electrolytic voltage for Ti at about −2.0 V and the specific resistance of the plating bath at 10 to 20 Ω·cm. The − electrical potential is applied to Ti on the basis of the above-described conditions in this electrolytic process, but the electrolytic deposition begins at the electrical potential for the Pt counter electrode of about −2.0 V to deposit the Pt particles on the surface of the surface of the Ti substrate, thereby making the platinum black plating progress. In the present preferred embodiment, the direct current is regulated so as to be supplied within a range of 80 to 90 mA in order to obtain such an electrolytic voltage. However, the resistance of the plating bath is low, so that a partition portion (not shown) provided with a plurality of small through holes is formed within the plating bath so that the interelectrode resistance R may be increased to obtain the desired electrolytic voltage. Subsequently, when the direct current is applied, an electrical field produced between the electrodes is narrowed by means of the small through holes. Thus, the interelectrode resistance R is increased, so that the suitable electrolytic voltage can be obtained in spite of the considerably reduced resistance of the plating both to closely deposit the Pt particles on the surface 3a of Ti.

Figure 2D:
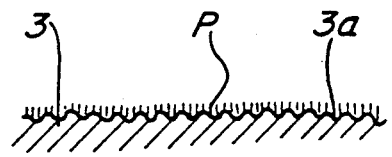

Accordingly, the plating of platinum black on Ti, which had been relatively impossible, becomes possible. A reaction at this time is expressed by a reaction formula $Pt^{4+} + 4e^- \rightarrow Pt$. The reaction formula indicates that platinum ions formed by the electrolysis in the electrolytic bath catch electrons to deposit Pt particles P on Ti, whereby the surface 3a of the electrodes are covered with the deposited Pt particles P to form the platinum black plated layer (refer to FIG. 2(d)). During this time, since the surface 3a of Ti is roughened to an extent of hundreds of meshes by the pretreatment, a coating is formed so that the Pt particles P may be adhered into small holes and the like on the surface 3a of Ti, whereby the cladding of the platinum black plated layer is strengthened. If Ti, which has been subjected to the platinum black plating in the above-described manner, is used as the electrode of the conductivity meter, the polarization phenomenon can be greatly reduced. Thus, the measurement can be appropriately conducted in the case where a solution having a high conductivity is measured. It is still necessary that the loss coefficient $D = 2\pi f \cdot C \cdot R$ is increased in order to reduce the polarization phenomenon, but the condenser portion C capable of increasing the surface area of the electrodes is made variable in the present preferred embodiment. Thus, the surface area of electrodes in the sensor portion is increased to hundreds of time, so that the loss coefficient D is increased and the polarization phenomenon is greatly reduced. Since the value of resistance of even a solution having a high conductivity can be appropriately measured, the conductivity can be accurately measured from the value of resistance.

As above described, in a conductivity meter according to the present invention, titanium, which is subjected to the platinum black plating, is used as the electrode material of the electrodes, so that the condenser portion relating to an increase of the surface area of the electrodes can be increased. Thus, the polarization phenomenon leading to an error of measurement can be reduced to measure the value of resistance of the solution with high accuracy, thereby accurately measuring the conductivity. Accordingly, a range of measurable conductivity can also be extended, so that a conductivity meter superior in versatility can be provided.

In addition, since titanium is inexpensive, the cost of production of the conductivity meter can be reduced. Furthermore, since the lead wires can be easily connected with titanium, the conventional problem relating to the connection of lead wires, which has occurred in the case where the lead wires are connected with the platinum electrodes, can be eliminated.

In addition, titanium is easily processed in the production of the electrodes, and a surface of titanium can be subjected to a pretreatment and then preelectrolysis, followed by plating in its platinum black plating, so that a strong platinum black plated coat can be formed on the surface of the electrodes.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a conductivity meter having electrodes, the improvement comprising:
    an electrode having an electrode substrate including titanium, the titanium material having an inner layer of a surface configuration resulting from a hot acid bath treatment of 3-N-HCL and an outer surface layer, deposited on the inner layer, of a platinum black plating.

2. The invention of claim 1 wherein the inner layer surface configuration has a roughness number of approximately 1,000.

3. The invention of claim 2 wherein the surface configuration is characterized as being immersed in the acid bath for approximately three hours at a temperature of 90° C. to 100° C.

4. In a conductivity meter having electrodes, the improvement comprising:
    an electrode having an electrode substrate of a material selected from a group consisting of titanium, titanium alloys, nickel, and stainless steel, the substrate material having an inner layer of a surface configuration resulting from a hot acid bath treatment, and an outer surface layer, deposited on the inner layer, of a platinum black plating.

5. The invention of claim 4, wherein the inner layer surface configuration has a roughness number of approximately 1,000.

6. In a conductivity meter having electrodes, the improvement comprising:
    an electrode having an electrode substrate including titanium, the titanium material having an inner layer of a surface configuration resulting from a hot acid bath treatment of 3-N-HCL for approximately three hours at a temperature of 90° C. and then subject to a subsequent pre-electrolysis procedure to remove hydrogen gas and a reduction process to remove any oxidation, the resultant surface configuration has a roughness number of approximately 1,000; and
    an outer surface layer, deposited across the entire inner layer, of a platinum black plating which is plated in a 3% aqueous solution of a chloroplatinic acid at approximately 60° C. for approximately 20 minutes at a constant current of approximately 80 mA.

* * * * *